United States Patent [19]

Walker et al.

[11] 4,144,277

[45] Mar. 13, 1979

[54] DEHYDROGENATION OF HYDROCARBONS WITH ZINC TITANATE CATALYST

[75] Inventors: Darrell W. Walker; Floyd E. Farha, Jr., both of Bartlesville, Okla.

[73] Assignee: Phillips Petroleum Company, Bartlesville, Okla.

[21] Appl. No.: 844,932

[22] Filed: Oct. 27, 1977

Related U.S. Application Data

[63] Continuation-in-part of Ser. No. 743,196, Nov. 19, 1976, abandoned.

[51] Int. Cl.$^2$ .............................................. C07C 5/36
[52] U.S. Cl. ........................... 260/666 A; 260/680 R; 260/683 R; 260/683.3; 252/461; 252/475

[58] Field of Search ..................... 260/680, 683.3, 683, 260/666 A; 423/598; 252/475, 461

[56] References Cited

U.S. PATENT DOCUMENTS 2,279,198   4/1942   Huppke .............................. 208/134

Primary Examiner—Veronica O'Keefe

[57] ABSTRACT

A process is used to dehydrogenate organic compounds to a higher degree of unsaturation by contacting in a first step, the organic compound with a calcined zinc titanate catalyst. In the second step, the catalyst is contacted with oxygen essentially in the absence of the dehydrogenatable organic compound. The first and second steps are repeated sequentially.

16 Claims, No Drawings

DEHYDROGENATION OF HYDROCARBONS WITH ZINC TITANATE CATALYST

This application is a Continuation-In-Part Application of Ser. No. 743,196 filed Nov. 19, 1976, now abandoned.

This invention relates to a process for dehydrogenation.

Dehydrogenation processes for the conversion of organic compounds to compounds having a higher degree of unsaturation include both thermal noncatalytic processes and catalytic processes. The former are characterized by undesirable side reactions, low order of conversion and yield and poor product selectivity. The catalytic processes are generally characterized by the particular catalytic material employed and the conditions under which the processes are operated, e.g., in the absence or presence of oxygen. While the number of such catalytic processes have achieved some measure of success, there is a continuing search to develop catalytic materials and processes which exhibit the high activity, high yield of desired product, high selectivity to desired product, and longevity and which keep undesirable side reactions to a minimum.

An object of the present invention is to provide a process for the catalytic dehydrogenation of organic compounds in the absence of free oxygen.

Other objects, aspects and advantages of this invention will be readily apparent to those skilled in the art from a reading of the specification and appended claims.

In accordance with the present invention there is provided a process for catalytically dehydrogenating a dehydrogenatable organic compound which process has alternate reaction periods and regeneration periods and comprises contacting an organic compound with a regenerable dehydrogenation catalyst, as described below, in the substantial absence of free oxygen under dehydrogenation conditions for a reaction period; and thereafter passing an oxygen-containing gas in contact with the catalyst under regeneration conditions for a regeneration period.

The process of this invention provides, with respect to known processes for oxidative dehydrogenation of organic compounds, several advantages: The cost of separating and purifying the products of the process of this invention is reduced. Selectivity to the desired product is increased. Less steam is required in the process of this invention.

The dehydrogenation catalyst employed in the process of the present invention is a calcined composition consisting essentially of zinc, titanium and sufficient oxygen to satisfy the valence requirements of zinc and titanium, wherein the atomic ratio of zinc to titanium is in the approximate range of 1.74:1 to 2.15:1, preferably about 2:1, which corresponds to zinc orthotitanate.

The catalyst can be prepared by intimately mixing suitable proportions of zinc oxide and titanium dioxide, and calcining the mixture in air at a temperature in the range of 650° to 1050° C., preferably from 675° to 975° C. It is presently preferred that the titanium dioxide used in preparing the catalyst have an average particle size of less than about 100 millimicrons.

The catalyst can also be prepared by coprecipitation from aqueous solutions of a zinc compound and a titanium compound. The aqueous solutions are mixed together and the hdyroxides ae precipitated by the addition of ammonium hydroxide. The precipitate is then washed, dried and calcined, as above.

The organic feedstocks which can be dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds include paraffins, olefins, cycloaliphatics and alkyl aromatic compounds having from 2 to 12 carbon atoms per molecule. Particularly suitable are paraffins and monoolefins, branched or unbranched. some examples of such applicable hydrocarbon feedstocks are ethane, propane, butane, isobutane, pentane, isopentane, hexane, 2-methylhexane, n-octane, n-dodecane, 1-butene, 2-butene, 2-methyl-butene-1, 2-methyl-butene-2, 2-hexene, 1-octene, 3-methylnonene-4, 1-dodecene, cyclohexane, and the like and mixtures thereof. Particularly appropriate is the conversion of ethane to ethylene, propane to propylene, butanes to butenes and butadiene, butenes to butadiene, and isopentane to isoamylenes and isoprene.

The process of this invention can be carried out by means of any apparatus whereby there is achieved an alternate contact of the catalyst with the gaseous phase containing the dehydrogenatable organic compound and thereafter of the catalyst with the oxygen-containing gaseous phase, the process being in no way limited to the use of a particular apparatus. The process of this invention can be carried out using a fixed catalyst bed, fluidized catalyst bed or moving catalyst bed. Presently preferred is a fixed catalyst bed.

In order to avoid any casual mixing of the organic compound and oxygen, provision can be made for intermediate supplemental injection of an inert purging gas, such as, for example, nitrogen, carbon dioxide or steam.

The time of reaction, i.e., dehydrogenation, for the dehydrogenatable organic compound can range from about 0.05 seconds to about 10 minutes, preferably from about 0.5 second to about 5 minutes and more preferably from abut 1 second to about 5 minutes.

The time of regeneration of the catalyst can range from 1 to 10 times the reaction period.

The temperature of the reaction can range from about 800° to about 1300° F. (426°–705° C.), preferably between 900° and 1200° F. (482°–650° C.), depending upon the nature of the organic feedstock.

The pressure of the reaction can range from about 0.05 to about 250 psia (5 to 1724 kPa).

The organic compound feed rate will generally be in the range of 50 to 5000 volumes of feedstock per volume of catalyst per hour, depending upon the feedstock, and the temperature and pressure employed, preferably from about 100 to about 2500. The presence of steam is frequently beneficial and steam:hydrocarbon mol ratios of up to 50:1 can be used, preferably from about 0.1:1 to about 20:1. An inert gaseous diluent, such as nitrogen or carbon dioxide, can also be used, and if used, will generally be in the same amounts as specified for the steam.

Steam can also be employed in admixture with the oxygen-containing gas during regeneration period. The amount of oxygen, from any source, supplied during the regeneration step will be in an amount sufficient to remove carbonaceous materials from the catalyst. Generally an amount in the range of about 1.5 to 5 times the volume of dehydrogenatable organic compound charged to the dehydrogenation step is employed The regeneration step is conducted at the same temperature and pressure recited for the dehyrogenation step, although somewhat higher temperatures can be used in some instances.

Thus, the operating cycle will include the successive steps of:

(1) Contacting the organic compound with the catalyst, resulting in the production of more unsaturated compounds. This step is optionally conducted in the additional presence of steam.
(2) Optionally, purging the catalyst with an inert gas.
(3) Contacting the catalyst with free oxygen.
(4) Optionally, purging the catalyst with an inert gas.
(5) Repeating step 1.

The following examples illustrate the invention:

EXAMPLE I

A zinc titanate catalyst was prepared by slurrying 162 grams of powdered zinc oxide, having an average particle size of about 130 microns, and 80 grams of finely divided titanium dioxide, having an average primary particle size of 30 millimicrons, in 1200 cc of water. The mixture was mixed in a high speed blender for 10 minutes. The resulting mixture was dried overnight in a forced draft oven at 220° F. The filter cake was divided into about 4 equal portions and each portion was calcined in air for 3 hours at the temperature indicated in Table I. Each portion, after cooling, was ground and screened to obtain 20–40 mesh particles (U.S. Sieve Series). A 2 cc sample of each composition was used in dehydrogenating isopentane in a fixed bed, low pressure automated testing unit.

Each run was conducted at 1100° F. (593° C.) at atmospheric pressure at an isopentane feed rate of about 250 GHSV. After charging the reactor with catalyst, the reactor and contents were brought up to reaction temperature in the presence of about 1250 GHSV steam and about 1250 GHSV nitrogen. Each cycle from this point on consisted of contacting the catalyst with a mixture of steam, nitrogen and air for a 6-minute regeneration period. Nominal GHSV of each component amounted to 1250, 1250 and 1800, respectively. Following regeneration, the air was cut off while steam and nitrogen at the same rates as before continued to flow for 6 minutes to purge out the air. The isopentane feed (250 GHSV) was then cut in and it was allowed to flow for 3 minutes to complete a 15-minute cycle. The hydrocarbon was carried into the reactor by a helium stream flowing at 930 GHSV.

The steam was condensed from the reactor effluent and the gas phase was analyzed by means of gas/liquid chromatography for isoprene, isoamylenes, carbon oxides and cracked products only. The analyzed values shown in Table I were obtained after 85 cycles.

Table I

| | Catalyst | | | | Yields, Products, Mole % | | | | |
|---|---|---|---|---|---|---|---|---|---|
| Run No. | Calcining Temp.° C. | Surface Area m²/g | Apparent Bulk Density g/cc | Conversion Mole % | Isoprene | Isoamylenes | Cracked | Carbon Oxides | Selectivity to Isoprene + Isoamylenes, % |
| 1 | 594 | 16.2 | 0.84 | 6.2 | 1.1 | 3.1 | 1.6 | 0.4 | 68 |
| 2 | 655 | 9.0 | 0.88 | 11.3 | 2.2 | 8.2 | 0.4 | 0.0 | 92 |
| 3 | 816 | 6.7 | 0.87 | 38.5 | 10.7 | 20.7 | 5.1 | 2.0 | 82 |
| 4 | 927 | 4.5 | 1.06 | 34.4 | 9.7 | 18.9 | 4.2 | 1.6 | 83 |
| 5 | 1010 | 1.2 | 1.38 | 7.6 | 1.6 | 4.0 | 1.6 | 0.4 | 74 |

The above results show that the calcining temperature used in preparing a zinc orthotitanate are important in obtaining active catalysts for isopentane dehydrogenation. Runs 3 and 4 show that the calcining temperatures ranging from about 800 to about 950° C. provide optimum catalysts for use in this process.

EXAMPLE II

A series of zinc titanate catalysts was prepared by blending powdered zinc oxide with commercially available titanium dioxide as described in Example I. Each titanium dioxide was characterized by a different average particle size. Each resulting blend, after drying overnight, was calcined in air for 3 hours at 816° C., cooled, ground and sieved to obtain 20–40 mesh particles for testing. Additionally, a coprecipitated catalyst was prepared by mixing an aqueous solution containing 118 grams of zinc nitrate hexahydrate and 71 grams of potassium titanium oxalate dihydrate and precipitating the hydroxides by increasing the pH of the solution to 8.3 by the addition of ammonium hydroxide. The precipitate was washed with hot, distilled water to essentially remove soluble salts, dried in the forced draft oven at 220° F., calcined in air for 3 hours at 816° C., cooled, ground and sieved to obtain 20–40 mesh particles for testing.

A 2 cc sample of each catalyst was individually charged to a reactor contained in the test unit used in the Example I.

Dehydrogenation of isopentane was conducted at atmospheric pressure at 1050° F. (566° C.) in a cyclic fashion as described in Example I. The flow rates of reactants and diluents were the same as used in Example I except that steam was absent in all the runs. Each effluent was analyzed by gas-liquid chromatography as before. The average particle size of the titanium dioxide used in preparing the catalyst and the results obtained are presented in Table II.

Table II

Effect of Zinc Titanate Preparation on Isopentane Dehydrogenation

| | | Catalyst | | Titania | | | Yields Products, Mole % | | | | Selectivity to Isoprene + Isoamylenes, % |
|---|---|---|---|---|---|---|---|---|---|---|---|
| Run No. | Catalyst Preparation[1] | Surface Area m²/g | Apparent Bulk Density g/cc | Particle Size Microns | Cycles | Conversion Mole % | Isoprene | Isoamylenes | Cracked | Carbon Oxides | |
| 1 | C | 10.6 | 0.65 | 2 | 141 | 34.8 | 11.3 | 20.6 | 2.2 | 0.7 | 92 |
| 2 | M | 6.6 | 0.88 | 0.030[3] | 141 | 42.7 | 11.4 | 28.1 | 2.3 | 0.8 | 93 |
| 3 | M | 2.3 | 1.00 | 140[4] | 57 | 5.3 | 0.8 | 1.3 | 3.1 | 0.2 | 40 |

Table II-continued

Effect of Zinc Titanate Preparation on Isopentane Dehydrogenation

| Run No. | Catalyst Preparation[1] | Catalyst Surface Area $m^2/g$ | Catalyst Apparent Bulk Density g/cc | Titania Particle Size Microns | Cycles | Conversion Mole % | Yields Products, Mole % Isoprene | Isoamylenes | Cracked | Carbon Oxides | Selectivity to Isoprene + Isoamylenes, % |
|---|---|---|---|---|---|---|---|---|---|---|---|
| 4 | M | 2.1 | 1.06 | 230[4] | 85 | 11.5 | 2.5 | 6.7 | 2.0 | 0.3 | 80 |

[1]C means coprecipitation; M means mixed.
[2]Not applicable.
[3]Flame hydrolyzed titanium dioxide.
[4]Commercially available powdered titanium dioxide.

The above results show that the most active zinc orthotitanate catalyst is obtained when such catalyst is prepared using a small particle size titania or by coprecipitation. When a comparatively large particle size titania is used, as shown in Runs 3 and 4, the results show that a much less active catalyst is produced, based on yield of products and conversion of feed.

EXAMPLE III

A zinc orthotitanate catalyst was prepared in the manner of Example I by slurrying a 40 gram portion of the same zinc oxide with a 20 gram portion of the titania used in Run 2 of Example II in 300 cc of distilled water for about 5 minutes in a high speed blender. The slurry was dried overnight at 120° C. in a forced draft oven and the cake was calcined for 3 hours at 816° C. The product, after cooling, was ground and screened to obtain 20-40 mesh particles. 2 cc portions of this catalyst were used in dehydrogenating propane in a fixed bed, low pressure automated testing unit. The catalyst had a surface area of 6.5 $m^2/g$ and an apparent bulk density of 0.96 g/cc.

The dehydrogenation was conducted in a cyclic fashion at atmospheric pressure as described in Example I, except that no steam was employed. In these tests, the flow rate of propane was 500 GHSV, the flow rate of nitrogen was 1000 GHSV and the flow rate of regeneration air was 1800 GHSV.

The reactor temperatures used, the number of cycles and the results obtained are presented in Table III. Each effluent was analyzed by gas-liquid chromatography as before.

Table III
Dehydrogenation of Propane Over Zinc Titanate Catalyst

| Run No. | 1 | 2 |
|---|---|---|
| Reactor Temp. °F (°C.) | 1150 (621) | 1200 (649) |
| Products Mole %: | | |
| Methane | 2.0 | 3.6 |
| CO | 0.6 | 1.5 |
| $CO_2$ | 1.0 | 1.1 |
| Ethylene | 2.3 | 3.9 |
| Propylene | 62.4 | 64.1 |
| Propane | 31.7 | 25.8 |
| Conversion Mole %: | 68.3 | 74.2 |
| Selectivity To Propylene, %: | 91 | 86 |
| Cycles: | 364 | 392 |

The above results show that zinc orthotitanate converts propane primarily to propylene under the reaction conditions employed.

Reasonable variations and modifications, which will be apparent to those skilled in the art, can be made in this invention without departing from the spirit and scope thereof.

We claim:

1. A process for catalytically dehydrogenating a dehydrogenatable hydrocarbon feedstock having at least one

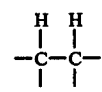

grouping which comprises:
contacting said feedstock with a regenerable dehydrogenation catalyst in the substantial absence of free oxygen under dehydrogenation conditions wherein said regenerable dehydrogenation catalyst is prepared by calcining a mixture of zinc oxide and titanium dioxide at a temperature in the range of from about 650° to about 1050° C.

2. A process according to claim 1 wherein said catalyst consists essentially of zinc, titanium and combined oxygen.

3. A process according to claim 2 wherein the atomic ratio of zinc to titanium in said catalyst is in the approximate range of 1.74:1 to 2.15:1 and the amount of oxygen is sufficient to satisfy the valence requirements of said zinc and said titanium.

4. The process according to claim 1 wherein said dehydrogenatable hydrocarbon feedstock is contacted with said catalyst under dehydrogenation conditions for a reaction period in the range of about 0.05 second to 10 minutes.

5. A process of claim 1 wherein following the reaction period of said dehydogenatable hydrocarbon feedstock with said regenerable dehydrogenation catalyst, said catalyst is thereafter regenerated by contacting said catalyst with an oxygen-containing gas under regeneration conditions.

6. A process according to claim 5 wherein said catalyst is contacted for a regeneration period ranging from about 1 to 10 times the length of the dehydrogenation reaction period.

7. A process according to claim 5 wherein steam is additionally present in admixture with said oxygen-containing gas during regeneration.

8. The process according to claim 1 wherein said feedstock is a dehydrogenatable hydrocarbon having 2 to 12 carbon atoms per molecule.

9. A process according to claim 1 wherein said catalyst is zinc orthotitanate.

10. A process according to claim 1 wherein the reaction temperature is in the range of about 426° to 705° C.

11. A process according to claim 1 wherein the pressure is between 0.05 and 250 psia.

12. A process according to claim 1 wherein said reaction period is in the approximate range of about 0.5 second to 5 minutes.

13. A process according to claim 5 further comprising the intermediate step of purging said catalyst after regeneration with an inert gas before reuse thereof for the dehydrogenation of said dehydrogenatable hydrocarbon feedstock.

14. A process according to claim 1 wherein said catalyst is calcined at a temperature in the approximate range of 675° to 975° C.

15. A process according to claim 1 wherein said titanium dioxide has an average particle size of less than 100 millimicrons.

16. A process according to claim 1 wherein said titanium dioxide has an average particle size of about 30 millimicrons.

* * * * *